United States Patent [19]

Harnisch

[11] 3,968,119
[45] July 6, 1976

[54] VIC-TRIAZOLE COMPOUNDS

[75] Inventor: Horst Harnisch, Cologne, Germany

[73] Assignee: Bayer Aktiengesellschaft, Leverkusen, Germany

[22] Filed: Jan. 4, 1974

[21] Appl. No.: 430,931

[30] Foreign Application Priority Data
Jan. 5, 1973   Germany............................ 2300488

[52] U.S. Cl...................... 260/308 A; 252/301.26; 252/301.29; 260/146 R; 260/240 C; 260/287 K; 260/287 CF; 260/288 CE; 260/289 R; 260/293.58; 260/308 R; 260/310 R; 260/310 C; 260/343.2 R
[51] Int. Cl.².............. C07D 487/04; C07D 491/04
[58] Field of Search................................ 260/308 A

[56] References Cited
UNITED STATES PATENTS
3,657,266   4/1972   Kirchmayr...................... 260/308 A
3,839,333   10/1974   Dorlars et al................... 260/308 A OTHER PUBLICATIONS
Beck et al., Chem. Abstracts, vol. 78, Abstract No. 111330n (1973).

*Primary Examiner*—Alton D. Rollins
*Attorney, Agent, or Firm*—Plumley and Tyner

[57] ABSTRACT

Vic-triazole compounds of the formula

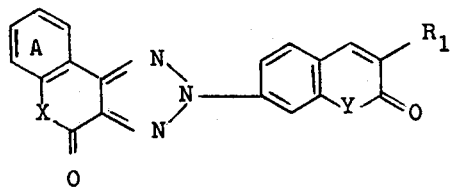

wherein
  X and Y stand for O or NR,
  $R_1$ stands for a mononuclear aromatically carbocyclic or aromatically heterocyclic radical,
  R stands for hydrogen, a (possibly substituted alkyl, aralkyl, cycloalkyl, aryl or alkoxycarbonyl radical, and
    wherein the aromatic and heterocyclic radicals may contain further non-chromophoric substituents with the exception of the nitro-group, and
  A may additionally be fused by a 5- or 6-membered carbocyclic ring,
    are useful as optical brightening agents for organic materials.

1 Claim, No Drawings

VIC-TRIAZOLE COMPOUNDS

The subject matter of the invention is fluorescent, almost colourless vic-triazole compounds of the general formula

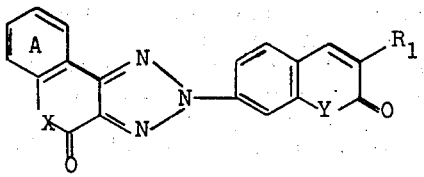

I wherein
X and Y stand for O or NR,
$R_1$ stands for a mononuclear, aromatically carbocyclic or aromatically heterocyclic radical,
R stands for hydrogen, a (possibly substituted) alkyl, aralkyl, cycloalkyl, aryl or alkoxycarbonyl radical, and
   wherein the aromatic and heterocyclic radicals may contain further non-chromophoric substituents with the exception of the nitro group, and
A may additionally be fused by a 5- or 6-membered carbocyclic ring,
processes for their preparation, and their use as optical brightening agents.

Mononuclearly aromatic-carbocyclic radicals $R_1$ are, in particular, phenyl radicals which may be substituted by nonchromophoric substituents with the exception of the nitro group. Corresponding aromatically heterocyclic radicals $R_1$ are, above all, 5- and 6-membered heterocyclic compounds, in particular 5-membered, which contain 1 to 3 nitrogen atoms, such as pyrrole, pyrazole, imidazole, 1,2,3-triazoles and 1,2,4-triazoles which are attached via an N-atom and may be substituted by non-chromophoric substituents with the exception of the nitro group.

Non-chromophoric substituents for the aromatic-carbocyclic and aromatic-heterocyclic radicals $R_1$ or for the ring A are, for example, alkyl radicals, in particular those with 1-4 C atoms, such as methyl, chloromethyl, trifluoromethyl, ethyl, isopropyl, tert.-butyl; aralkyl radicals, preferably those with 7-10 C atoms, such as benzyl, p-methylbenzyl, p-chlorobenzyl and phenylethyl; aryl radicals, such as phenyl; cycloalkyl radicals, in particular those with 5-7 C atoms, for example cyclohexyl; halogen atoms, for example fluorine, chlorine and bromine; alkylsulphonyl radicals, in particular with 1-4 C atoms in the alkyl radical, for example methyl, ethyl and β-hydroxyethylsulphonyl; carboxylic acid or sulphonic acid groups or their functional derivatives, in particular their alkyl esters with 1-4 C atoms or (possibly substituted by alkyl or alkylene radicals) amides, the alkyl radicals containing preferably 1-4 C atoms and the alkylene radicals containing preferably 4-6 C atoms, e.g. carboxylic acid methyl ester, ethyl ester, n-butyl ester, sulphonic acid diethyl amide, piperidide, n-butyl amide, sulphonic acid amide; cyano radicals and alkoxy radicals, in particular those with 1- 4 C atoms, preferably methoxy and ethoxy.

The alkyl radicals R contain preferably 1-5 C atoms and may carry substituents such as hydroxy, $C_1$-$C_4$-alkoxy, amino, $C_1$ - $C_4$-alkylamino, $C_2$ - $C_8$-dialkylamino, cyano, carboxy, carboxylic acid alkyl esters with 1-4 C atoms in the alkyl radical, carboxylic acid amide, halogens, such as fluorine, chlorine and bromine, a saturated 5- or 6-ring attached via nitrogen, heterocyclic compounds, such as pyrrolidine, piperidine, morpholine or piperazine. Aralkyl radicals R are preferably benzyl radicals, aryl radicals R are preferably phenyl radicals and cycloalkyl radicals R are preferably cyclohexyl radicals. Alkoxycarbonyl radicals contain preferably 1-5 C atoms, such as methoxycarbonyl, ethoxycarbonyl.

A particularly valuable group of compounds within the scope of the general formula I is characterized by the formula

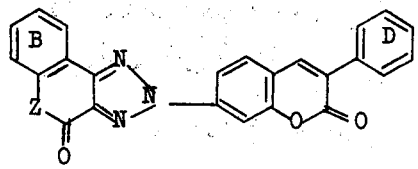

II wherein
Z stands for O or $NR_2$,
$R_2$ stands for hydrogen, an alkoxycarbonyl group with 1-5 C atoms or a (possibly substituted) alkyl group with 1-4 C atoms,
B may be fused by a benzene ring or substituted by $C_1$-$C_4$— alkyl, halogen or $C_1$-$C_4$alkoxy, and
D may be substituted by $C_1$-$C_4$-alkyl, halogen, cyano or carboxylic acid $C_1$-$C_4$-alkyl esters or carboxylic acid amide.

Suitable substituents on the alkyl group for $R_2$ are phenyl, hydroxy, $C_1$-$C_4$-alkoxy, chlorine, cyano, carboxy, carbonamide, carboxylic acid $C_1$-$C_4$-alkyl esters.

Preferred substituents on the rings B and D are methyl, ethyl and chlorine. Particularly preferred are compounds in which Z stands for oxygen.

The compounds according to the invention can be prepared according to various processes.

One of the processes is characterised in that a compound of the formula

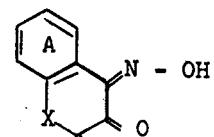

III or

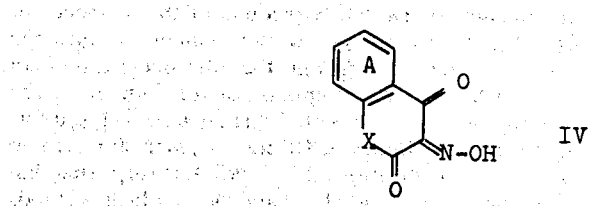

IV wherein
A and X possess the meaning stated above is condensed with a 7-hydrazino compound of the formula

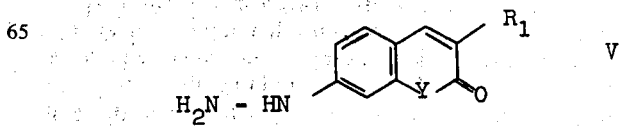

V wherein
R₁ and Y have the meaning stated above and the coumarin radical may contain further non-chromophoric substituents with the exception of the nitro group
to give the oximinohydrazone compound of the formula

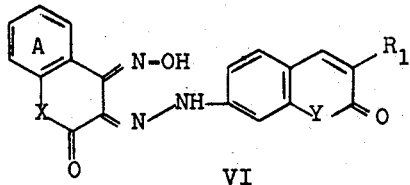

VI or

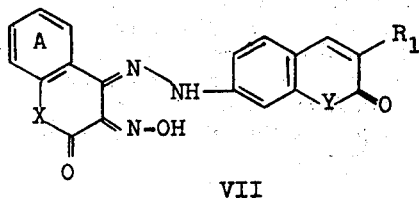

VII and subsequently either directly cyclised in dehydrating manner to give the compound of the formula I or first dehydrogenated in cyclising manner to give the corresponding N-oxide, and the intermediate product reduced to give the compound of the formula I. The carrying out can be effected analogously to the information given in Deutsche Offenlegungsschrift (German Published Specification) 2 045 795. It is surprising that the coumarin compounds III and IV, in which X stands for oxygen, which in general are far less stable to ring openings than are 3-aryl-coumarins, such as V, are not split in the reaction with the hydrazino compounds V.

The compounds of the formulae III and IV are obtained by nitrositing the corresponding 3- or 4-hydroxycoumarins and 3- or 4-hydroxycarbostyrils by, for example, dissolving the 4-hydroxycoumarin or 4-hydroxycarbostyril in an equivalent amount of solution of sodium hydroxide, adding an equivalent amount of sodium nitrite solution and running this mixture at 0°–5°C into excess 10% strength hydrochloric acid.

3-hydroxycoumarins or 3-hydroxycarbostyrils are nitrosited in glacial acetic acid.

Hydroxycoumarins suitable for the preparation of III or IV are for example the following compounds: 3-hydroxy-coumarin, 4-hydroxy-coumarin, 3-hydroxy-6-methylcoumarin, 4-hydroxy-6-methyl-coumarin, 3-hydroxy-7-methyl-coumarin, 3-hydroxy-7-ethyl-coumarin, 4-hydroxy-8-methyl-coumarin, 4-hydroxy-5-methyl-coumarin, 4-hydroxy-6-chloro-coumarin, 4-hydroxy-6-tertiary-butyl-coumarin, 4-hydroxy-6-bromo-coumarin, 4-hydroxy-6-methoxy-coumarin, 4-hydroxy-7-methoxy-coumarin, 4-hydroxy-6-phenyl-coumarin, 4-hydroxy-6-cyclohexyl-coumarin, 4-hydroxy-6-benzyl-coumarin, 4-hydroxy-6-fluoro-coumarin, 4-hydroxy-5,6-benzo-coumarin, 3-hydroxy-7,8-benzo-coumarin.

Hydroxy-carbo-styrils suitable for the preparation of III or IV are for example the following compounds:
4-hydroxy-1-methyl-carbostyril, 3-hydroxy-1-ethyl-carbostyril, 4-hydroxy-1-n-butyl-carbostyril, 4-hydroxy-1,6-dimethyl-carbostyril, 4-hydroxy-1-β-cyano-ethyl-carbostyril, 4-hydroxy-1-β-aminocarbonyl-ethyl-carbostyril, 4-hydroxy-1-β-carboxy-ethylcarbostyril, 4-hydroxy-1-β-hydroxyethyl-carbostyril, 4-hydroxy-1-β-chloroethyl-carbostyril, 4-hydroxy-1-γ-dimethyl-amino-n-propyl-carbostyril, 4-hydroxy-1-methyl-6-tertiary-butyl-carbostyril, 4-hydroxy-1-methyl-6-methoxy-carbostyril, 4-hydroxy-1-methyl-7-chloro-carbostyril, 4-hydroxy-1-ethyl-7,8-benzo-carbostyril, 4-hydroxy-1-phenyl-carbostyril, 4-hydroxy-1-benzylcarbostyril, 4-hydroxy-1-cyclohexyl-carbostyril.

7-hydrazino-coumarin compounds of the formula V are known and can be prepared according to the method of working stated in Deutsche Offenlegungsschrift (German Published Specification) 1 670 999. As examples, there are mentioned:
7-hydrazino-3-phenyl-coumarin, 7-hydrazino-3-(p-tolyl)-coumarin, 7-hydrazino-3-(p-chlorophenyl)-coumarin, 7-hydrazino-3-phenyl-6-methyl-coumarin, 7-hydrazino-3-(p-n-butylphenyl)-coumarin, 7-hydrazino-3-(p-bromophenyl)-coumarin, 7-hydrazino-3-pyrazol-1'-yl-coumarin, 7-hydrazino-3-(3'-methylpyrazol-1'-yl)-coumarin, 7-hydrazino-3-(4'-chloropyrazol-1'-yl)-coumarin, 7-hydrazino-3-(1',2',-3'-triazol-1'-yl)-coumarin, 7-hydrazino-3-(1',2',4'-triazol-1'-yl)-coumarin, 7-hydrazino-3-(p-methoxyphenyl)-coumarin, 7-hydrazino-3-(p-ethoxy-phenyl)-coumarin, 7-hydrazino-3-(p-cyano-phenyl)-coumarin and 7-hydrazino-3-(p-ethoxy-phenyl)-coumarin.

7-hydrazino-carbostyrils of the formula V can be easily prepared from the 7-amino-carbostyrils by diazotisation and reduction according to customary procedures. 7-amino-carbostyrils are known for example from Deutsche Offenlegungsschriften 1 519 467 and 1 594 847.

A second, particularly simple process for the preparation of compounds of the formula I is characterised in that 7-amino-coumarins or -carbostyrils of the formula

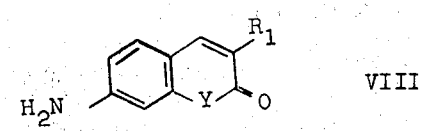

VIII wherein
R₁ and Y possess the meaning stated above and the coumarin ring may contain further non-chromophoric substituents with the exception of the nitro group,
are diazotised, coupled to a 3- or 4-amino-coumarin- or -carbostyril compound of the formula

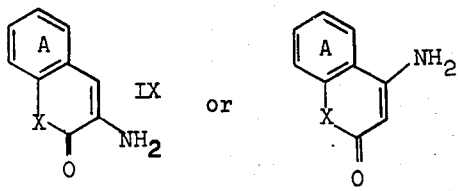

wherein
  A and X have the meaning stated above, and wherein the reaction with the compound IX is preferred,
and the obtained o-amino-azo compounds of the formulae

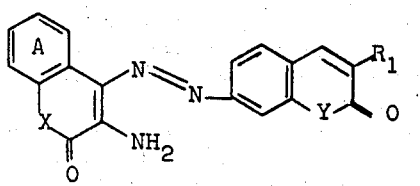

XI or

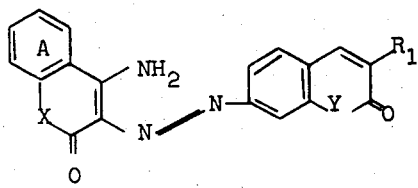

XII are cyclised in dehydrogenating manner to give the compound of the formula I. Sulphonic-acid-group-containing compounds of the formula I are advantageously obtained by subsequent sulphonation of unsulphonated compounds of the formula I.

7-amino-coumarins or -carbostyrils of the formula VIII are known, for example, from Deutsche Offenlegungsschriften (German Published Specifications) 1 670 999, 1 594 847 and 1 519 467. The diazotisation and coupling of the compounds of the formula VIII can be carried out according to the method of working of Deutsche Offenlegungsschriften (German Published Specifications) 1 795 152 or 1 470 242.

3-amino-coumarins (IX, X=O) are obtained by hydrolysis, under mild conditions, of the 3-acetylaminocoumarins accessible by condensation of salicylaldehydes with aminoacetic acid in acetic anhydride/sodium acetate according to the information given in Archiv der Pharmazie 296, 396 or in the Journal of the Indian Chemical Society 48, 371 (1971).

4-amino-coumarins and -carbostyrils of the formula X and 3-aminocarbostyrils (IX, X=NR) can be prepared by amination of the corresponding halogen compounds, in particular of the chlorine compounds, according to the method of working stated in Chemical Abstracts 58 (1963) 9010c.

Suitable amino-coumarins IX and X are for example 3-amino-coumarin, 4-amino-coumarin, 3-amino-6-methyl-coumarin, 4-amino-6-methyl-coumarin, 3-amino-6-chloro-coumarin, 4-amino-6-bromo-coumarin, 3-amino-6-fluoro-coumarin, 3-amino-6-methoxy-coumarin, 3-amino-6-ethoxy-coumarin, 3-amino-6-tert.-butyl-coumarin, 3-amino-6-phenyl-coumarin, 3-amino-6-cyclohexyl-coumarin, 4-amino-7-methyl-coumarin, 3-amino-7-ethyl-coumarin, 4-amino-5, 6-benzo-coumarin, 3-amino-7,8-benzo-coumarin, 4-amino-7,8-tetramethylene-coumarin.

Suitable 3-amino- and 4-amino-carbostyrils of the formulae IX and X are e.g. 3-amino-carbostyril, 4-amino-carbostyril, 4-amino-1-methyl-carbostyril, 4-amino-1,8-dimethyl-carbostyril, 4-amino-6-methoxy-1-ethyl-carbostyril, 4-amino-1-β-methoxy-ethyl-7-methyl-carbostyril.

The cyclisation of the compounds XI and XII to give triazoles is expediently carried out in a hydrophilic, non-oxidisable organic solvent, such as dimethyl formamide, pyridine or picoline bases, in such a manner that the o-amino-azo dyestuff of the formula XI or XII is heated with a suitable oxidation agent, for example a copper(II) salt such as copper(II) sulphate, chloride, acetate, carbonate or naphthenate in the presence of water and nitrogen bases such as ammonia, diethanolamine or, in particular, pyridine, or with an alkali metal hypochlorite such as sodium hypochlorite. Expediently, the work is carried out in the temperature range of 20°–110°C, preferably at 80°–100°C.

A further form of carrying out the triazolisation consists in reacting the o-amino-azo dyestuff of the formula XI or XII according to the method of working stated in Deutsche Offenlegungsschrift (German Published Specification) 1 803 636 with thionylaniline in high-boiling solvents, for example dichlorobenzene, to give I.

A third process for the preparation of the compounds of the formula I is characterised in that a compound of the formula

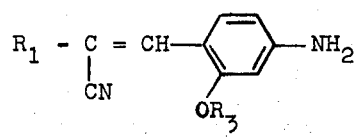

XIII wherein $R_1$ has the meaning stated above, the benzene ring may contain further non-chromophoric substituents with the exception of the nitro group, and $R_3$ stands for an alkyl group with 1-4 C atoms is diazotised and coupled to an amino compound of the formula IX or X, the obtained o-amino-azo compound is cyclised in dehydrogenating manner to give the triazole compound of the formula

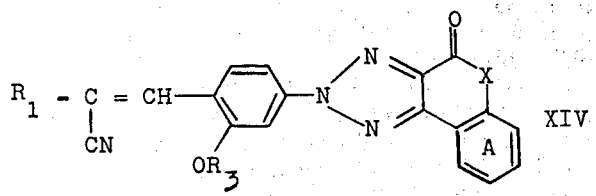

wherein $R_1$, $R_3$, A and X have the meaning stated above, the group $OR_3$ is subsequently hydrolysed and further treated in an acid medium, with coumarin cyclisation and formation of I. The carrying out of this process takes place according to the method of working described in Deutsche Offenlegungsschrift (German Published Specification) 1 909 182.

A fourth process for the preparation of compounds of the formula (I) is characterised in that compounds of the formula VIII are diazotised and coupled to a compound of the formula

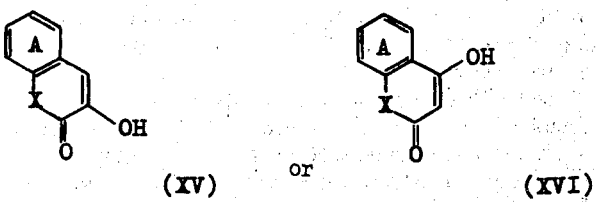

wherein

A and X have the meaning stated above and reacted with at least 1 mole of ammonium acetate and in the presence of copper (II) salts. Preferentially, the reaction is carried out with 2 – 2.5 moles of copper-(II) salts or with air and catalytic amounts of copper(II) salts in solvents at a temperature of 0°–150°C.

The process is particularly suitable for compounds of the formulae (XV) or (XVI) in which X stands for oxygen.

The compounds according to the invention are suitable for the optical brightening of organic materials. Depending on the substituent, they are particularly suitable for specific substrates. They serve for the optical brightening of high-molecular-weight hydrophobic organic material, above all for the brightening of synthetic organic plastics, particularly in the spinning mass, i.e. synthetic substances obtainable by polymerisation, polycondensation or polyaddition, such as polyolefins, e.g. polyethylene or polypropylene; further, of polyvinyl chloride but, above all, of polyesters, particularly polyesters of aromatic polycarboxylic acids with polyhydric alcohols, such as polyterephthalic acid glycol esters, synthetic polyamides such as nylon-6 and nylon-66 but also cellulose esters, such as cellulose esters, such as cellulose acetates. Compounds of the formula I which contain sulphonic acid groups are particularly suitable for the optical brightening of polyamides and polyurethanes.

The optical brightening of the high-molecular-weight hydrophobic organic material is effected for example by incorporating into it small amounts of optical brighteners according to the invention, preferably 0.001 to 1%, with reference to the material to be brightened, optionally together with other substances, such as plasticisers, stabilisers or pigments. The brighteners can for example be worked into the synthetic substances after the former have been dissolved in plasticisers, such as dioctylphthalate, or together with stabilisers, such as dibutyl tin dilaurate or sodium pentaoctyltripolyphosphate, or together with pigments, as for example titanium dioxide. Depending on the nature of the material to be brightened, the brightener can also be dissolved in the monomers before polymerisation, in the polymeric mass or together with the polymer in a solvent. The thus pretreated material is then brought into the desired final form by processes known per se, such as calendering, pressing, extrusion, coating, casting and, above all, spinning and stretching. The brighteners can also be worked into finishes, for example into finishes for textile fibres, such as polyvinyl alcohol, or into resins, for example resin precondensates, as for example methylol compounds of ethyleneurea, which serve for textile treatment.

High-molecular-weight organic material can also be brightened in the form of fibres. For brightening these fibre materials, an aqueous dispersion of the compounds according to the invention of the formula I is advantageously used. The brightener dispersion in this case preferably has a content of 0.005–0.5% of compound according to the invention of the formula I, with reference to the fibre material. The dispersion may additionally contain auxiliary materials, such as dispersing agents, for example condensation products of fatty alcohols (or alkyl phenols) having 10–18 carbon atoms with 15–25 moles of ethylene oxide, or condensation products of alkylmonoamines (or polyamines) having 16–18 carbon atoms with at least 10 moles of ethylene oxide; organic acids, such as formic, oxalic or acetic acid, washing agents, swelling agents, such as di- or tri-chlorobenzenes, wetting agents, such as sulphosuccinic acid alkyl ester, bleaching agents, such as sodium chlorite, peroxides or hyposulphites and, optionally, brightening agents of other classes, as for example derivatives of stilbene which have an affinity for cellulose.

Brightening of the fibre material with the aqueous brightener dispersion is effected either in the exhaust process at temperatures of preferably 30°–150°C or in the padding process. In the latter case, the goods are impregnated with a for example 0.2 to 0.5% strength brightener dispersion and they are finished for example by dry or moist heat treatment, e.g. by steaming at 2 atmospheres or, after drying has been effected, by brief dry heating to 180°–220°C, the fabric (according to circumstances) being also heat-set at the same time. Finally, the fibre material thus treated is washed and dried.

High-molecular-weight organic material optionally brightened according to the invention has a pure white, predominantly bluish fluorescent appearance.

EXAMPLE 1

27.3 g 3-phenyl-7-aminocoumarin hydrochloride are suspended in 180 g glacial acetic acid, 30 g of concentrated hydrochloric acid are added and cooling is effected, followed by diazotisation (for 45 minutes) at 10°C with 30% strength (by volume) sodium nitrite solution. The nitrite excess is destroyed by addition of a little amidosulphonic acid. The diazonium salt suspension obtained is added in about 20 minutes at 10°–15°C to a solution of 16.1 g 3-aminocoumarin in 200 ml pyridine. Stirring is effected for a further 30 minutes. The obtained dyestuff of the formula

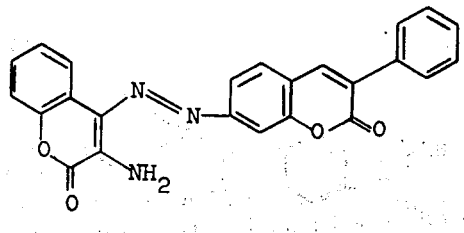

(1)

which in dimethyl formamide or o-dichlorobenzene shows a quite weakly reddish, intensely blue fluorescence.

In analogous manner, with the use of the corresponding 7-amino- and 3-amino-coumarins the following compounds of the formula below are prepared.

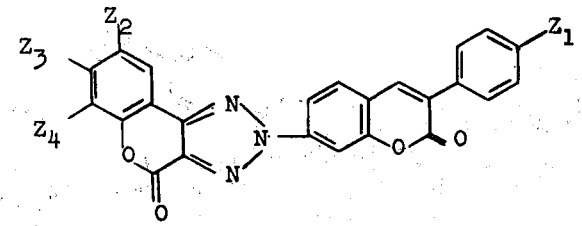

| Compound No. | $Z_1$ | $Z_2$ | $Z_3$ | $Z_4$ | Fluorescence colour in dimethyl formamide |
|---|---|---|---|---|---|
| (3) | H | $CH_3$ | H | H | neutral blue |
| (4) | $COOC_2H_5$ | H | $CH_3$ | H | neutral blue |
| (5) | H | H | H | $CH_3$ | neutral blue |
| (6) | H | Cl | H | H | slightly greenish blue |
| (7) | H | H | Cl | H | slightly greenish blue |
| (8) | $CH_3O$ | Br | H | H | strongly greenish blue |
| (9) | H | F | H | H | neutral blue |
| (10) | H | $C_6H_{11}$ | H | H | slightly greenish blue |
| (11) | H | $OCH_3$ | H | H | greenish blue |
| (12) | CN | $C_6H_5$ | H | H | greenish blue |
| (13) | H | Cl | H | Cl | greenish blue |
| (14) | Cl | H | H | H | greenish blue |
| (15) | H | $(CH_3)_3C$ | H | H | neutral blue | can be cyclised (without intermediate isolation) in the same reaction medium. For this purpose, 60 ml of water and 60 g of crystallised copper sulphate are added and the mixture is heated to 90°–95°C for 6 hours; substantial decolorising occurs. The crystalline precipitate is filtered off hot, with suction, washed with methanol until the run-off is colourless, and dried at 70°C in a vacuum. 27 g of a compound of the formula

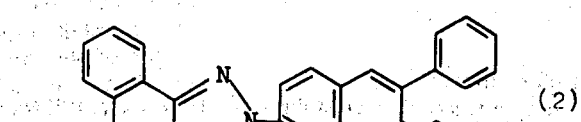

(2)

are obtained.

It is purified by recrystallisation, first from 550 ml dimethyl formamide, and another recrystallisation from 400 ml o-dichlorobenzene with the use of bleaching earth, washing with methanol being effected in each case. Compound 2 is a slightly yellowish crystal powder

EXAMPLE 2

29.3 g 7-acetylamino-3-p-tolylcoumarin (prepared from 4-acetylaminosalicylidene-aniline, p-tolylacetic acid, sodium acetate and acetic anhydride according to the information given in Deutsche Offenlegungsschrift (German Published Specification) 1 519 471, first Example) are suspended in 300 ml glacial acetic acid, 50 g of concentrated hydrochloric acid are added, and heating to reflux temperature is effected for 60 minutes. The mixture is cooled to 5°C and the amino compound is diazotised with 30% strength (by volume) sodium nitrite solution at 5°C (45 minutes). The nitrite excess is destroyed with amidosulphonic acid. The diazonium salt suspension obtained is added in about 20 minutes, at 10°–15°C, to a solution of 16.1 g 4-aminocoumarin in 200 ml pyridine. Stirring is effected for a further 30 minutes. The obtained dyestuff of the formula

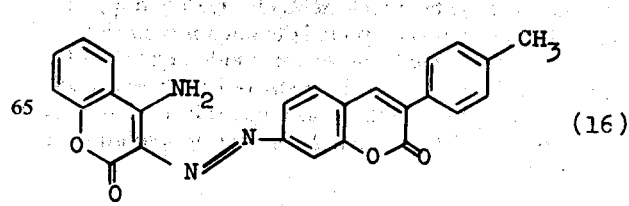

(16)

can without intermediate isolation be further processed in the same reaction medium.

For this purpose, 60 ml of water and 70 g of crystallised copper sulphate are added and the mixture is heated to 70°–75°C for 6 hours; substantial decolorising occurs. The crystalline precipitate is cooled, filtered off with suction, washed with methanol until the run-off is colourless, and dried at 70°C in a vacuum. 21 g of a compound of the formula

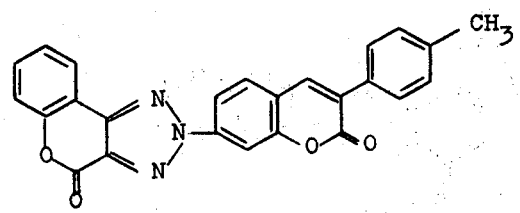
(17)

are obtained.

It is purified as in Example 1. Compound 17 is a yellowish crystal powder which in dimethyl formamide or chlorobenzene shows an intense blue fluorescence.

In analogous manner, with the use of the corresponding 7-acetylamino- and 4-amino-coumarins the following compounds of the formula

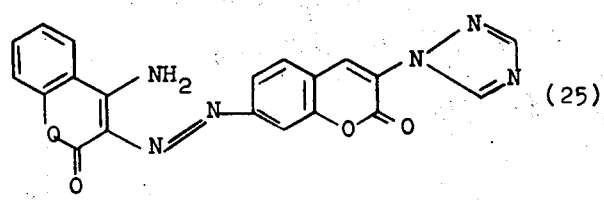

are prepared.

16.1 g 3- or 4-aminocoumarin in 200 ml pyridine. Stirring is effected for a further 30 minutes. The dyestuffs of the formulae

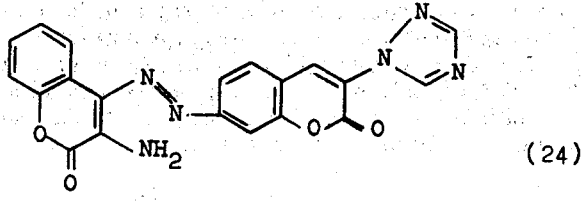
(24)

and (25)

can without intermediate isolation be further processed in the same reaction medium. For this purpose, 60 ml of water and 70 g of crystallised copper sulphate are added and the mixture is heated to 90°C for 6 hours; substantial decolorising occurs. The crystalline precipitate is cooled, filtered off with suction, washed with methanol until the run-off is colourless, and dried at 70°C in a vacuum. 19 g of a compound of the formula

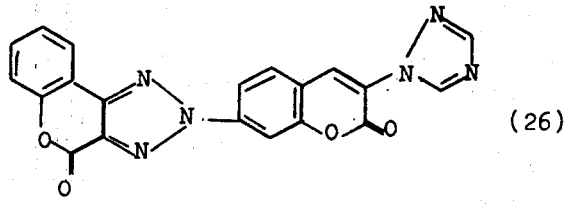
(26)

| Compound No. | $Z_6$ | $Z_2$ | $Z_3$ | $Z_4$ | $Z_5$ | $Z_1$ | Fluorescence colour in dimethyl formamide |
|---|---|---|---|---|---|---|---|
| (18) | H | H | H | H | $CH_3$ | $C_2H_5O$ | greenish blue |
| (19) | $CH_3$ | H | H | H | H | H | neutral blue |
| (20) | —CH=CH—CH=CH— | | H | H | H | H | greenish blue |
| (21) | H | H | —CH=CH—CH=CH | H | H | H | greenish blue |
| (22) | H | H | H | H | H | $(CH_3)_3C$ | neutral blue |
| (23) | H | —$CH_2$—$CH_2$—$CH_2$—$CH_2$— | | H | H | H | slightly greenish blue |

EXAMPLE 3

30 g 7-acetylamino-3-(1',2',4'-triazol-1'-yl)-coumarin (prepared according to the information given in Deutsche Offenlegungsschrift (German Published Specification) 1 919 181) are heated to the boil under reflux in a mixture of 220 g glacial acetic acid and 50 g of concentrated hydrochloric acid for 30 minutes and cooled. The amino compound obtained is diazotised at 5°C with 30% strength (by volume) sodium nitrite solution. The nitrite excess is destroyed with amidosulphonic acid. The resulting diazonium salt suspension is added at 10°–15°C in about 20 minutes to a solution of are obtained.

It is purified by recrystallisation, from from 100 ml dimethyl formamide, and another recrystallisation from 1,2,4-trichlorobenzene with the use of bleaching earth, washing with methanol being effected in each case. Compound 26 is a yellowish crystal powder which in dimethyl formamide shows a slightly reddish-blue fluorescence.

In analogous manner, with the use of the corresponding starting compounds the following compounds of the formula

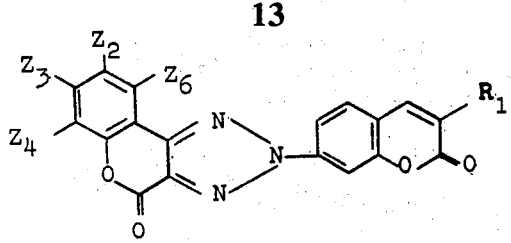

are prepared.

29 g 7-hydrazino-3-phenylcoumarin hydrochloride and 19.1 g of the compound of the formula 34 are heated to 70°–80°C in 215 ml ethyleneglycol-monomethyl ether and 45 g of 60% strength acetic acid for 6 hours. After cooling, the yellowish-brown crystalline precipitate is filtered off with suction, washed with methanol and dried at 50°C in a vacuum. 38 g of a compound of the formula

| Compound No. | $R_1$ | $Z_6$ | $Z_2$ | $Z_3$ | $Z_4$ | Fluorescence colour in dimethyl formamide |
|---|---|---|---|---|---|---|
| (27) | ![pyridazinyl-Cl] | H | H | H | H | weakly reddish blue |
| (28) | ![pyridazinyl-CH3] | H | OCH₃ | H | H | greenish blue |
| (29) | ![triazinyl] | H | CH₃ | H | H | neutral blue |
| (30) | ![tetrahydrophthalazinyl] | H | H | CH₃ | H | Weakly reddish blue |
| (31) | ![triazinyl] | CH₃ | H | H | H | weakly reddish blue |
| (32) | ![triazinyl] | H | H | H | CH₃ | weakly reddish blue |
| (33) | ![pyridazinyl-CH3-Cl] | —CH=CH—CH=CH— | | H | H | greenish blue |

EXAMPLE 4

97.2 g 4-hydroxycoumarin are dissolved in a solution of 24 g sodium hydroxide in 600 ml of water, a solution of 45 g sodium nitrite in 300 ml of water is added and cooling to 0°C is effected. This solution is run in 15 minutes into a mixture of 240 ml of concentrated hydrochloric acid and 1.8 l of water at 0°–5°C. A yellow crystalline precipitate forms. This is filtered off with suction, washed with water and dried at 40°C in a vacuum. 114.5 g of a compound of the formula

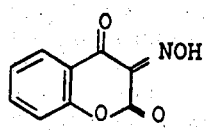 (34)

are obtained.

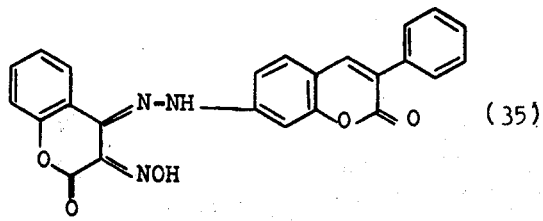 (35)

are obtained. These are warmed to 70°C with 33 g of anhydrous potassium acetate in 26 ml acetic anhydride for 30 minutes, with stirring, heated to reflux for 8 hours and cooled. the crystalline precipitate is filtered off with suction, washed with methanol, hot water and again with methanol and subsequently recrystallised from o-dichlorobenzene with the use of bleaching earth. 18 g of a compound of the formula 2 are obtained.

EXAMPLE 5

If the procedure according to the information given in Example 4 is followed but, instead of compound 34, an equivalent amount (20.4 g) 4-oxo-3-isonitroso-1-methylcarbostyril is used, the dyestuff of the formula

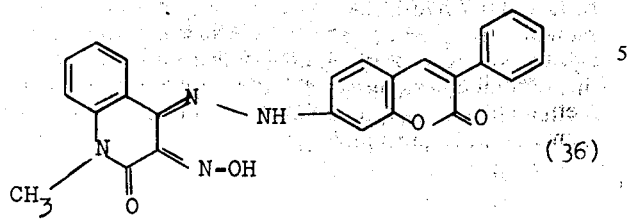

(36)

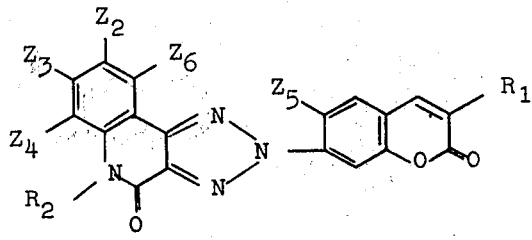

are prepared.

| Compound No. | $Z_6$ | $Z_2$ | $Z_3$ | $Z_4$ | $R_2$ | $R_1$ | $Z_5$ | Fluorescence colour in dimethyl formamide |
|---|---|---|---|---|---|---|---|---|
| (38) | $CH_3$ | H | H | H | $CH_3$ | —⟨⟩—$CH_3$ | H | neutral blue |
| (39) | H | $CH_3O$ | H | H | $CH_2CH_2OH$ | —⟨⟩ | H | greenish blue |
| (40) | H | Cl | H | H | $CH_2$—$CH_2CN$ | —⟨⟩ | $CH_3$ | slightly greenish |
| (41) | H | $CH_3$ | H | H | $CH_2$—⟨⟩ | —⟨⟩—Cl | H | greenish blue |
| (42) | H | H | $CH_3$ | H | —$(CH_2)_3CH_3$ | —⟨⟩ | H | slightly greenish blue |
| (43) | H | H | H | H | —$CH_2$—$CH_2$—COOH | —⟨⟩ | H | neutral blue |
| (44) | H | $(CH_3)_3C$ | H | H | —$CH_2$—$CH_2$—$CONH_2$ | —⟨⟩ | $C_2H_5$ | slightly greenish blue |
| (45) | H | H | H | H | $C_2H_5$ | N⟨N⟩N | H | slightly reddish blue |
| (46) | H | H | H | H | $CH_3$ | N⟨N⟩Cl | H | slightly reddish blue |
| (47) | H | H | —CH=CH—CH=CH— | | $C_2H_5$ | —⟨⟩ | H | greenish blue | is obtained and, from this, after treatment with potassium acetate/acetic anhydride, 21 g of a compound of the formula

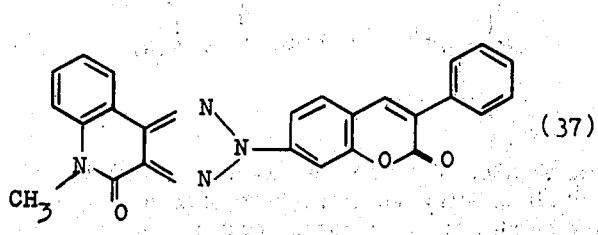

(37)

Compund 37 is a yellowish crystal powder which, dissolved in dimethyl formamide, shows a strong blue fluorescence. In analogous manner, with the use of the corresponding starting compounds the following compounds of the formula

EXAMPLE 6

5.9 g 1-methyl-3-phenyl-7-aminocarbostyril (prepared according to the information given in the German Offenlegungschrift (Published Specification) 1 469 225, Example 1) are dissolved in 50 ml glacial acetic acid, with heating. The solution after addition of 30 ml of concentrated hydrochloric acid, is cooled and the amino compound is diazotised at 0°–5°C by addition of 30 percent by volume sodium nitrite solution. After destruction of the nitrite excess with amidosulphonic acid, the diazonium salt suspension is added at 10°–15°C in about 15 minutes to a solution of 3.8 g 4-aminocoumarin in 80 ml pyridine. Stirring is effected for a further 60 minutes. The dyestuff of the formula

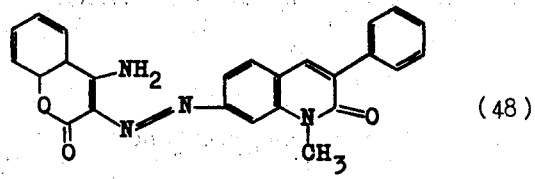

(48)

is filtered off with suction, washed with water, suspended in 150 ml pyridine, 10 g of copper acetate are added and heating to the boil under reflux for 3 hours is effected. After cooling, the crystalline precipitate is filtered off with suction, washed with water and recrystallized from dimethyl formamide. 4 g of a compound of the formula

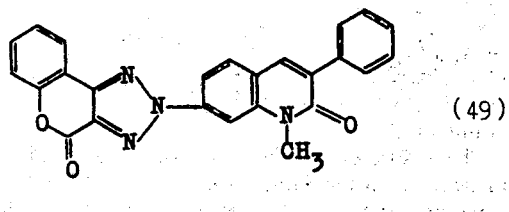

are obtained.

For further purification, 49 is recrystallised from o-dichlorobenzene with the use of bleaching earth. Compound (49) is a yellowish crystal powder which in dimethyl formamide shows an intensely blue fluorescence.

If, instead of 4-aminocoumarin, an equivalent amount of 4-amino-1-methylcarbostyril is used as coupling component, there is obtained, after triazolising with copper acetate, the compound of the formula

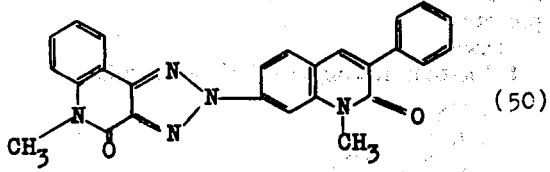

(50) is likewise a yellowish crystal powder which fluoresced intensely blue in dimethyl formamide.

In analogous manner, with the use of the corresponding starting compounds the following compounds of the formula

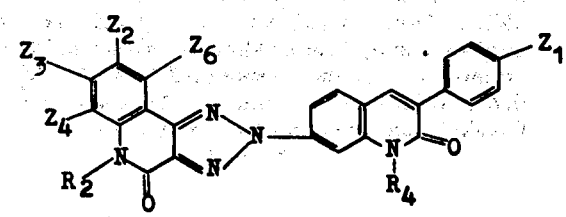

are prepared.

| Compound No. | $R_2$ | $R_4$ | $Z_4$ | $Z_3$ | $Z_2$ | $Z_6$ | $Z_1$ | Floursecence colour in dimethyl formamide |
|---|---|---|---|---|---|---|---|---|
| (51) | $CH_3-(CH_2)_3$ | $COOC_2H_5$ | H | H | H | | H | neutral blue |
| (52) | $COOCH_3$ | $C_2H_5$ | H | H | $CH_3$ | H | H | neutral blue |
| (53) | $CH_3$ | $CH_3$ | H | H | Cl | H | $CH_3$ | greenish blue |
| (54) | $HO-CH_2-CH_2$ | $CH_3$ | $CH_3$ | H | H | H | $CCH_3$ | greenish blue |
| (55) | $NC-CH_2-CH_2$ | $NC-CH_2-CH_2$ | H | $CH_3$ | H | H | Cl | greenish blue |

EXAMPLE 7

10 g of a compound of the formula 2 are introduced at room temperature into 50 g of 96% strength sulphuric acid and stirring is effected until all is dissolved. Subsequently, 10 parts of 30% strength oleum are added dropwise at 20°–30°C. The mixture is stirred for about 8 hours at 30°–40°C until a specimen is completely soluble in hot water and the mixture is then discharged on to 100 ml of water and 100 g of ice. The crystalline precipitate is filtered off with suction, taken up in 100 ml of water, neutralised with solution of sodium hydroxide, salted out by addition of dilute solution of sodium chloride, filtered off with suction, washed with 5% strength solution of sodium chloride and dried at 70°C in a vacuum. A yellow watersoluble crystal powder is obtained which shows in dimethyl formamide a slightly reddish blue fluorescence.

EXAMPLE 8

A solution of 1 g of the brightener 2 in dimethyl formamide is prepared. Of this stock solution 20 ml are added to a mixture of 380 ml of water, 0.3 g of a commercial alkylpolyglycol ether and 0.2 g trichlorobenzene as carrier. 10 g of a polyester fabric are introduced into this bath at 30°C. The temperature is increased to 125°C in 30 minutes, using a closed dyeing apparatus, and dyeing is effected at this temperature for 45 minutes. Cooling to 60°C is then effected. The fabric is rinsed and dried. It shows a brilliant brightening which is highly fast to light.

Similarly good brightening effects are attained when, instead of compound 2, one of the following brighteners is used: 3, 4, 5, 6, 9, 15, 17, 19, 22, 33, 37, 38.

EXAMPLE 9

2 g of a 50% strength paste of cyclohexane peroxide in dibutyl phthalate, 1 g rutile and 0.2 g of the compound 17 are added to a mixture of 70 g of a polyester (which is prepared from adipic acid and ethylene glycol) and 30 g styrene. The mixture is poured out into a mould and hardened at about 90°–100°C. The resulting moulded article shows a very good brightening with excellent fastness to light.

EXAMPLE 10

100 g polyester granulate of polyterephthalic acid ethyleneglycol ester are intimately mixed with 0.01 g of the compound 37 and melted at 280°–300°C. After the spinning of the mass through conventional spinnerets polyester fibres brightened in outstanding light-fast manner are obtained.

A similarly good and light-fast brightening effect is obtained when, instead of compound 37, compound 17 is used.

EXAMPLE 11

In an alloy steel autoclave which is provided with a stirrer, gas introduction tube, a vacuum device, a descending condenser and a heating jacket 388 g terephthalic acid dimethyl ester, 300 g ethylene glycol and 0.4 g antimony oxide are heated to 200°C while pure nitrogen is blown through, and the mixture is kept at this temperature for 3 hours, with methanol being distilled off. A solution of 0.4 g of the compound of the formula 2 in 50 ml ethylene glycol is then run in at 190°C with exclusion of air, and the temperature is increased to 280°C. in 1 hour, with stirring; glycol distils off. Vacuum is then applied and the pressure is slowly reduced to 0.2 mm Hg. After 3 hours at 280°C/0.2 mm Hg the polycondensation has ended. The polymer is forced out through the nozzle at the bottom with nitrogen. Monofilaments produced from this show a brilliant white aspect of high fastness to light.

EXAMPLE 12

Cellulose triacetate fibres (Arnel) are introduced in a liquor ratio 1:30 into an aqueous bath which contains, per liter, 1 g of a commercial interface-active paraffin sulphonate and 0.07 g of the compound of the formula (17) as brightening agent. The bath is heated to 125°C in 30 minutes in a closed dyeing apparatus, kept at this temperature for 40 minutes and cooled. The fibres are rinsed and dried. They show a brilliant brightening effect of high fastness to light.

EXAMPLE 13

Polyamide fibres of ε-caprolactam are introduced at 60°C in a liquor ratio 1:30 into an aqueous bath which contains 0.07 g of brightener prepared according to Example 7. The bath is heated to 95°C for 60 minutes. The fibres are then rinsed and dried. They show a good brightening effect.

EXAMPLE 14

54.6 g 3-phenyl-7-aminohydrochloride are diazotised according to the information given in Example 1 and coupled at 10°C to 32.4 g 4-hydroxycoumarin or 3-hydroxycoumarin in 260 ml pyridine. The bright red dyestuff of the formula

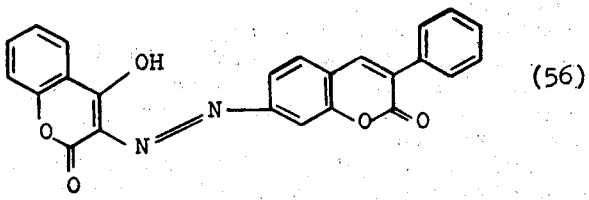

(56)

or

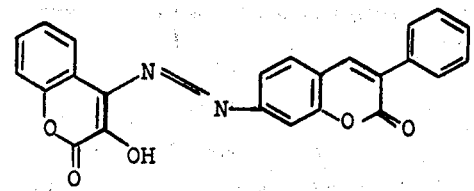

(57)

is obtained.

This is filtered off with suction, washed with alcohol and recrystallised from about 2 liters of N-methylpyrrolidone. Yield 76 g 56 and 74.5 g 57, 41g of the dyestuff of the formula 56 or 57 are dissolved under reflux in 1.1 liters of N-methylpyrrolidone, cooled to 110°C, 55 g of crystallised copper sulphate and 77 g ammonium acetate are added in about 20 minutes; heating to the boil under reflux is effected for 3 hours, followed by cooling. Stirring together with water is effected, the crystalline precipitate is filtered off with suction, washed with water then with alcohol and dried at 70°C in a vacuum. 33 g of the compound of the formula 2 are obtained. In analogous manner, with the use of corresponding starting materials the compounds of the formula 3, 5 to 15, 17 to 23, 26, 28 to 32, 49 are also prepared.

I claim:

1. Vic-triazole compound of the formula

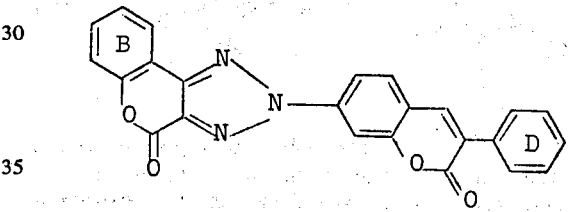

wherein

B is unsubstituted; substituted by a fused unsubstituted benzene ring; monosubstituted by fluoro, chloro, bromo, $C_1$-$C_4$-alkyl or $C_1$-$C_4$-alkoxy; or disubstituted by fluoro, chloro, or bromo; and D is unsubstituted or monosubstituted by $C_1$-$C_4$-alkyl, fluoro, chloro, bromo, cyano, carboxylic acid $C_1$-$C_4$-alkyl ester, or carboxylic acid amide.

* * * * *